US009586215B2

(12) United States Patent
Stearns et al.

(10) Patent No.: US 9,586,215 B2
(45) Date of Patent: Mar. 7, 2017

(54) AVOIDANCE OF BOUNCING AND SPLASHING IN DROPLET-BASED FLUID TRANSPORT

(71) Applicant: Labcyte Inc., Sunnyvale, CA (US)

(72) Inventors: Richard G. Stearns, Felton, CA (US); Stephen J. Hinkson, Berkeley, CA (US)

(73) Assignee: Labcyte Inc., Sunnyvale, CA (US)

( * ) Notice: Subject to any disclaimer, the term of this patent is extended or adjusted under 35 U.S.C. 154(b) by 0 days.

(21) Appl. No.: 13/752,077

(22) Filed: Jan. 28, 2013

(65) Prior Publication Data
US 2013/0193243 A1 Aug. 1, 2013

Related U.S. Application Data

(63) Continuation of application No. 12/944,364, filed on Nov. 11, 2010, now Pat. No. 8,389,295, which is a
(Continued)

(51) Int. Cl.
B05B 5/00 (2006.01)
B01L 3/02 (2006.01)
G01N 35/10 (2006.01)

(52) U.S. Cl.
CPC ............ *B05B 5/005* (2013.01); *B01L 3/0268* (2013.01); *G01N 35/1009* (2013.01);
(Continued)

(58) Field of Classification Search
CPC . B05B 5/005; Y10T 436/2575; B01L 3/0268; B01L 2300/0819; B01L 2300/0829;
(Continued)

(56) References Cited

U.S. PATENT DOCUMENTS 3,380,584 A 4/1968 Fulwyler
4,308,547 A 12/1981 Lovelady et al.
(Continued)

FOREIGN PATENT DOCUMENTS

CN 1289271 A 3/2001
EP 1 245 274 10/2002
(Continued)

OTHER PUBLICATIONS

Amemiya et al., *IS&T 's NIP 13: International Conference on Digital Printing Technologies*, 1997, pp. 698-702.
(Continued)

*Primary Examiner* — Brian R Gordon
(74) *Attorney, Agent, or Firm* — Jones Day

(57) ABSTRACT

A system for fluid transport is provided where a quantity of fluid is held in a reservoir. A droplet generator is employed to generate droplets from the fluid, for example a nozzle-based system or a nozzleless system such as an acoustic ejection system. A generated droplet has a trajectory whereby it arrives at a target. A circuit is used to modify one or more characteristics of the generated droplet in a way which increases the likelihood that the droplet will not splash or bounce when it arrives at the target. The circuit may in different embodiments control the speed of the droplet or the Weber number of the droplet. The circuit may create an electric field in an area of space where the droplet passes. The circuit may charge the droplet by causing it to contact ions.

27 Claims, 5 Drawing Sheets

Related U.S. Application Data continuation of application No. 11/080,024, filed on Mar. 14, 2005, now abandoned.

(52) U.S. Cl.
CPC .. *G01N 35/1074* (2013.01); *B01L 2300/0819* (2013.01); *B01L 2300/0829* (2013.01); *B01L 2400/027* (2013.01); *B01L 2400/0436* (2013.01); *B01L 2400/0487* (2013.01); *G01N 2035/1034* (2013.01); *Y10T 436/2575* (2015.01)

(58) Field of Classification Search
CPC ....... B01L 2400/027; B01L 2400/0436; B01L 2400/0487; G01N 35/10009; G01N 35/1074; G01N 2035/1034
USPC .................................. 436/174, 180; 250/288
See application file for complete search history.

(56) References Cited

U.S. PATENT DOCUMENTS

| | | | |
|---|---|---|---|
| 4,748,043 A | 5/1988 | Seaver et al. | |
| 5,041,849 A | 8/1991 | Quate et al. | |
| 5,541,627 A | 7/1996 | Quate | |
| 5,798,779 A | 8/1998 | Nakayasu et al. | |
| 6,015,880 A | 1/2000 | Baldeschwieler et al. | |
| 6,063,339 A | 5/2000 | Tisone et al. | |
| 6,287,520 B1 | 9/2001 | Parce et al. | |
| 6,368,562 B1 | 4/2002 | Yao | |
| 6,402,282 B1 | 6/2002 | Webb | |
| 6,416,164 B1 | 7/2002 | Stearns et al. | |
| 6,710,335 B2* | 3/2004 | Ellson et al. ................ | 250/288 |
| 6,713,021 B1 | 3/2004 | Shvets et al. | |
| 6,797,945 B2 | 9/2004 | Berggren et al. | |
| 6,869,551 B2 | 3/2005 | Lee et al. | |
| 6,938,995 B2 | 9/2005 | Mutz et al. | |
| 6,995,024 B2 | 2/2006 | Smith et al. | |
| 7,179,423 B2 | 2/2007 | Bohm et al. | |
| 7,211,223 B2 | 5/2007 | Fouillet et al. | |
| 7,275,807 B2* | 10/2007 | Van Tuyl ......................... | 347/46 |
| 7,332,347 B2 | 2/2008 | Li et al. | |
| 7,405,072 B2 | 7/2008 | Mutz et al. | |
| 7,429,359 B2* | 9/2008 | Reichel et al. ............... | 422/510 |
| 8,389,295 B2 | 3/2013 | Stearns et al. | |
| 2002/0003177 A1 | 1/2002 | O'Connor et al. | |
| 2002/0037375 A1 | 3/2002 | Ellson et al. | |
| 2002/0037579 A1 | 3/2002 | Ellson et al. | |
| 2002/0090720 A1 | 7/2002 | Mutz et al. | |
| 2002/0092366 A1 | 7/2002 | Brock et al. | |
| 2002/0094582 A1 | 7/2002 | Williams et al. | |
| 2002/0109084 A1 | 8/2002 | Ellson et al. | |
| 2002/0125424 A1 | 9/2002 | Ellson et al. | |
| 2002/0140118 A1 | 10/2002 | Lee | |
| 2002/0142049 A1 | 10/2002 | Lee | |
| 2002/0151085 A1 | 10/2002 | Zaffaroni et al. | |
| 2002/0155231 A1 | 10/2002 | Ellson et al. | |
| 2002/0158027 A1 | 10/2002 | Moon et al. | |
| 2002/0168297 A1 | 11/2002 | Shvets et al. | |
| 2003/0012892 A1 | 1/2003 | Lee et al. | |
| 2003/0080208 A1 | 5/2003 | Williams et al. | |
| 2003/0101819 A1 | 6/2003 | Mutz et al. | |
| 2003/0148538 A1 | 8/2003 | Ng | |
| 2003/0150257 A1 | 8/2003 | Mutz et al. | |
| 2003/0175163 A1 | 9/2003 | Shvets et al. | |
| 2003/0211620 A1 | 11/2003 | Labudde et al. | |
| 2003/0230344 A1 | 12/2003 | Ellson et al. | |
| 2004/0014029 A1 | 1/2004 | Mutz et al. | |
| 2004/0091398 A1 | 5/2004 | Gilbert et al. | |
| 2004/0101445 A1 | 5/2004 | Shvets et al. | |
| 2004/0120855 A1* | 6/2004 | Reichel et al. ................ | 422/67 |
| 2004/0134933 A1 | 7/2004 | Mutz et al. | |
| 2004/0151635 A1 | 8/2004 | Leproust et al. | |
| 2005/0036920 A1 | 2/2005 | Gilbert | |
| 2005/0153458 A1 | 7/2005 | Van den Engh | |
| 2005/0232823 A1 | 10/2005 | Brock et al. | |
| 2006/0263264 A1* | 11/2006 | Bohm et al. ................ | 422/100 |

FOREIGN PATENT DOCUMENTS

| | | |
|---|---|---|
| EP | 1 295 643 | 3/2003 |
| WO | WO 99/34931 | 7/1999 |

OTHER PUBLICATIONS

Dell'Aversana et al., "When Liquids Stay Dry," Physics Today, Jan. 1998, pp. 38-41.
Hagesaether, "Coalescence and break-up of drops and bubbles," Ph.D. Thesis, Norwegian University of Science and Technology, pp. 1-209, Mar. 2002.
Jackson, J.D., *Classical Electrodynamics* (John Wiley & Sons, Inc., 1962), Chapters 1-4, pp. 1-131.
Orme, M. "Experiments on Droplet Collisions, Bounce, Coalescence and Disruption," Progress in Energy and Combustion Science, 23:65-79 (1997).
Patent Cooperation Treaty, International Search Report for PCT/US2006/009236, mailed Jul. 6, 2006.
Patent Cooperation Treaty, Written Opinion of the International Searching Authority for PCT/US2006/009236, mailed Jul. 6, 2006.
Rhim, "Measurements of thermophysical properties of molten materials from drop oscillation and rotation," Spacebound Materials, (3) (2000) downloaded from www.space.gc.ca/asc/pdf/2000_Rhim.pdf#search='surface%20tension%20charged%20drop'.
Strutt, Baron R., "On the equilibrium of liquid conducting masses charged with electricity," Phil. Mag., XIV:184-186 (1882).
Non final office action dated Apr. 22, 2011 for U.S. Appl. No. 12/944,364 (10 pages).
Non final office action dated Dec. 16, 2011 for U.S. Appl. No. 12/944,364 (11 pages).
Notice of allowance dated Nov. 6, 2012 for U.S. Appl. No. 12/944,364 (7 pages).
Non final office action dated Sep. 17, 2008 for U.S. Appl. No. 11/080,024 (12 pages).
Final office action dated Jun. 9, 2009 for U.S. Appl. No. 11/080,024 (19 pages).
Non final office action dated Feb. 12, 2012 for U.S. Appl. No. 11/080,024 (26 pages).
Communication from European Patent Office for EP 06 738 310.9 dated Aug. 19, 2015 (7 pages).
Communication from European Patent Office for EP 06 738 310.9 dated May 31, 2013 (4 pages).
Communication from European Patent Office for EP 06 738 310.9 dated Jun. 13, 2016 (4 pages).

* cited by examiner

AVOIDANCE OF BOUNCING AND SPLASHING IN DROPLET-BASED FLUID TRANSPORT

TECHNICAL FIELD

This application is a continuation of U.S. patent application Ser. No. 12/944,364, filed Nov. 11, 2010, which is a continuation of U.S. patent application Ser. No. 11/080,024, filed Mar. 14, 2005, both of which are incorporated by reference herein for all purposes.

BACKGROUND

There exists a need in pharmaceutical, biotechnological, medical, and other industries to be able to quickly screen, identify, analyze, and/or process large numbers or varieties of fluids. As a result, much attention has been focused on developing efficient, precise, and accurate fluid handling methods. For example, automated robotic systems have been used in combination with precise registration technologies to dispense reagents through automated pick-and-place ("suck-and-spit") fluid handling systems. Similarly, some efforts have been directed to adapting printing technologies, particularly inkjet printing technologies, to form biomolecular arrays. For example, U.S. Pat. No. 6,015,880 to Baldeschwieler et al. is directed to array preparation using multistep in situ synthesis. Such synthesis may involve using inkjet technology to dispense reagent-containing droplets to a locus on a surface chemically prepared to permit covalent attachment of the reagent.

There are tradeoffs in the choice of a fluid transport system. For example, most fluid handling systems presently in use require that contact be established between the fluid to be transferred and an associated solid surface on the transferring device. Such contact typically results in surface wetting that causes unavoidable fluid waste, a notable drawback when the fluid to be transferred is rare and/or expensive. When fluid transport systems are constructed using networks of tubing or other fluid transporting conduits, air bubbles can be entrapped or particulates may become lodged in the networks. Nozzles of ordinary inkjet printheads are also subject to clogging, especially when used to eject a macromolecule-containing fluid at elevated temperatures, a situation commonly associated with such technologies. As a result, ordinary fluid transport technologies may produce improperly sized or misdirected droplets.

A number of patents have described the use of focused acoustic radiation to dispense fluids such as inks and reagents. For example, U.S. Pat. No. 4,308,547 to Lovelady et al. describes a liquid drop emitter that utilizes acoustic principles to eject droplets from a body of liquid onto a moving document to result in the formation of characters or barcodes thereon. A nozzleless inkjet printing apparatus is used such that controlled drops of ink are propelled by an acoustical force produced by a curved transducer at or below the surface of the ink. Similarly, U.S. Patent Application Publication No. 20020037579 to Ellson et al. describes a device for acoustically ejecting a plurality of fluid droplets toward discrete sites on a substrate surface for deposition thereon. U.S. Patent Application Publication No. 20020094582 to Williams describes technologies that employ focused acoustic technology as well. In contrast to inkjet printing devices, focused acoustic radiation may be used to effect nozzleless fluid ejection, and devices using focused acoustic radiation are not generally subject to clogging and the disadvantages associated therewith, e.g., misdirected fluid or improperly sized droplets.

Since fluids used in pharmaceutical, biotechnological, and other scientific industries may be rare and/or expensive, techniques capable of handling small volumes of fluids provide readily apparent advantages over those requiring relatively larger volumes. Typically, fluids for use in combinatorial methods are provided as a collection or library of organic and/or biological compounds. In many instances, well plates are used to store a large number of fluids for screening and/or processing. Well plates are typically of single piece construction and comprise a plurality of identical wells, wherein each well is adapted to contain a small volume of fluid. Such well plates are commercially available in standardized sizes and may contain, for example, 96, 384, 1536, or 3456 wells per well plate.

Transport of fluid droplets may be directed at an existing volume of fluid. For example, in any fluid transport system that employs discrete droplets, it may be desirable to use a number of smaller droplets to transport the fluid rather than a single larger droplet. Each droplet after the first will potentially impact an existing volume of fluid.

When a fluid droplet is directed at an existing volume of fluid, it is often desirable that the droplet coalesce with the existing volume. Instead of coalescing, a droplet may bounce or splash, which is often undesirable. Bouncing and splashing may also be undesirable when the droplets are directed at a solid target. For example, the target may be a well plate in which the droplet is supposed to be placed entirely in an identified individual well in accordance with the transfer protocol being employed, whereas splashing might cause a portion of the fluid in the droplet to fall into a different well instead.

Bouncing of droplets when they encounter a solid or an existing volume of fluid has been observed for many years. It is believed that the phenomenon involves not simply the droplet and the solid or volume of fluid but also a cushion of air between the droplet and the solid or volume. Precise predictions of when droplet bouncing and splashing will occur based on conventional fluid parameters such as viscosity and surface tension are often not within the capabilities of computational fluid mechanics, so that empirical investigation is a preferred method of analyzing questions which relate to droplet bouncing and splashing. A summary of certain empirical investigations is found in M. Orme, "Experiments on Droplet Collisions, Bounce, Coalescence and Disruption," *Progress in Energy and Combustion Science*, vol. 23, pp. 65-79, 1997, which contains a number of references to the literature.

SUMMARY OF THE INVENTION

The invention is in general a system for fluid transport. A quantity of fluid is held in a reservoir. A droplet generator is employed to generate droplets from the fluid, for example a nozzle-based system or a nozzleless system such as an acoustic ejection system. The droplet generator may or may not make contact with the fluid in order to generate the droplet. The droplet generator may be set up to move from one reservoir to another in order to be able to eject from more than one reservoir. In a common arrangement, a number of reservoirs form part of an integral structure, e.g., a well plate, and the structure is moved by suitable mechanical or electromechanical systems, potentially under computer control, into a suitable position with respect to the droplet generator.

The droplet generator is controlled by a controller, preferably electronic and connectable to computers through some communications system. The droplets after generation arrive at a target, which may be for example a well plate, a porous or non-porous surface, a substrate, or a structure which is to be coated by the droplets. A circuit controls one or more characteristics of the generated droplet, increasing the likelihood that the droplet will not splash or bounce on arriving at the target. This circuit may be controlled by the controller or may form part of the controller. The target may already have a quantity of fluid, and the droplet may coalesce with that quantity of fluid.

In certain preferred embodiments, the circuit for controlling one or more characteristics may control the speed of the droplet as it arrives at the target. The speed may be controlled in preferred ranges. In another embodiment, the circuit for controlling may control the Weber number of the droplet. In doing so, the circuit may control for example the diameter of the droplet or its velocity or both. In another preferred embodiment, the circuit may provide an electric field in an area of space through which the droplet passes. This electric field may result in polarization or charging of the droplet. In another preferred embodiment, the circuit may charge the droplet by causing it to contact ions.

The invention also encompasses methods for the transport of fluids. In these methods, a droplet is generated from a quantity of fluid in a reservoir. A trajectory of the droplet is controlled in such a way that it arrives at a target. One or more characteristics of the generated droplet are controlled so as to increase the likelihood that the droplet will not splash or bounce on arriving at the target.

BRIEF DESCRIPTION OF THE DRAWINGS

The invention is described in detail below with reference to the following drawings, wherein like reference numerals indicate a corresponding structure throughout the several views.

FIG. 1A shows the acoustic ejector acoustically coupled to a first reservoir and having been activated in order to eject a first droplet of fluid from within the reservoir toward a particular site on a substrate surface. FIG. 1B shows the acoustic ejector acoustically coupled to a second reservoir and having been activated to eject a second droplet of fluid from within the second reservoir.

DETAILED DESCRIPTION OF THE INVENTION

Figure 1A:
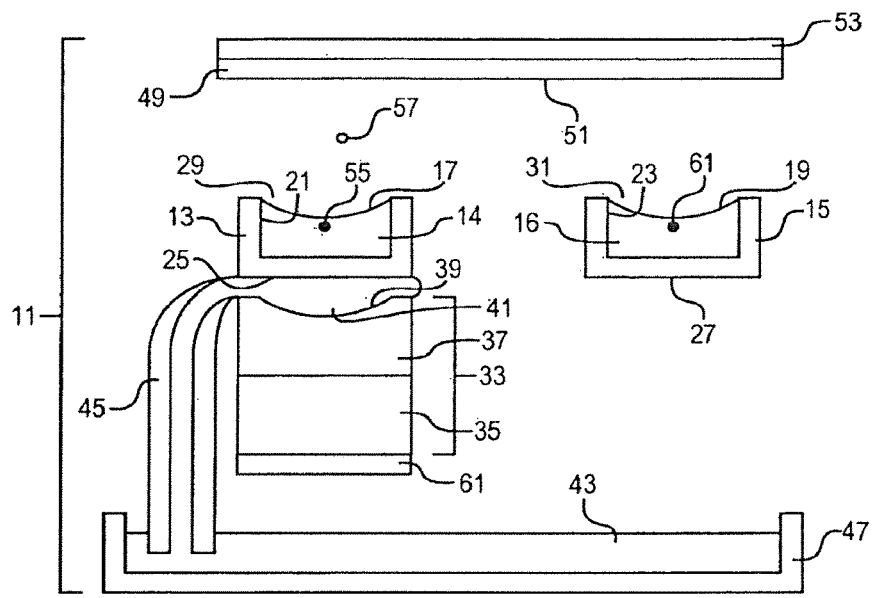
FIGS. 1A and 1B, collectively referred to as FIG. 1, schematically illustrate in simplified cross-sectional view the operation of a focused acoustic ejection device in the preparation of a plurality of features on a substrate surface.

Before describing the present invention in detail, it is to be understood that this invention is not limited to specific fluids, biomolecules, or device structures, as such may vary. It is also to be understood that the terminology used herein is for the purpose of describing particular embodiments only, and is not intended to be limiting.

It must be noted that, as used in this specification and the appended claims, the singular forms "a," "an," and "the" include both singular and plural referents unless the context clearly dictates otherwise. Thus, for example, reference to "a reservoir" includes a plurality of reservoirs as well as a single reservoir, reference to "a droplet" includes a plurality of droplets as well as single droplet, and the like.

In describing and claiming the present invention, the following terminology will be used in accordance with the definitions set out below.

The terms "acoustic coupling" and "acoustically coupled" as used herein refer to a state wherein an object is placed in direct or indirect contact with another object so as to allow acoustic radiation to be transferred between the objects without substantial loss of acoustic energy. When two items are indirectly acoustically coupled, an "acoustic coupling medium" is needed to provide an intermediary through which acoustic radiation may be transmitted. Thus, an ejector may be acoustically coupled to a fluid, e.g., by immersing the ejector in the fluid or by interposing an acoustic coupling medium between the ejector and the fluid, in order to transfer acoustic radiation generated by the ejector through the acoustic coupling medium and into the fluid.

The term "array" as used herein refers to a two-dimensional arrangement of features, such as an arrangement of reservoirs (e.g., wells in a well plate) or an arrangement of different moieties, including ionic, metallic, or covalent crystalline, e.g., molecular crystalline, composite, ceramic, vitreous, amorphous, fluidic, or molecular materials on a substrate surface (as in an oligonucleotide or peptidic array). Arrays are generally comprised of regular features that are ordered, as in, for example, a rectilinear grid, parallel stripes, spirals, and the like, but non-ordered arrays may be advantageously used as well. In particular, the term "rectilinear array" as used herein refers to an array that has rows and columns of features wherein the rows and columns typically, but not necessarily, intersect each other at a ninety-degree angle. An array is distinguished from the more general term "pattern" in that patterns do not necessarily contain regular and ordered features. Arrays typically but do not necessarily comprise at least about 4 to about 10,000,000 features, generally in the range of about 4 to about 1,000,000 features.

The terms "biomolecule" and "biological molecule" are used interchangeably herein to refer to any organic molecule that is, was, or can be a part of a living organism, regardless of whether the molecule is naturally occurring, recombinantly produced, or chemically synthesized in whole or in part. The terms encompass, for example, nucleotides, amino acids, and monosaccharides, as well as oligomeric and polymeric species, such as oligonucleotides and polynucleotides; peptidic molecules, such as oligopeptides, polypeptides, and proteins; saccharides, such as disaccharides, oligosaccharides, polysaccharides, and mucopolysaccharides or peptidoglycans (peptido-polysaccharides); and the like. The terms also encompass ribosomes, enzyme cofactors, pharmacologically active agents, and the like. Additional information relating to the term "biomolecule" can be found in U.S. Patent Application Publication No. 20020037579 to Ellson et al.

The term "capillary" is used herein to refer to a conduit having a bore of small dimension. Typically, capillaries for electrophoresis that are free standing tubes have an inner diameter in the range of about 50 to about 250 µm. Capillaries with extremely small bores integrated to other devices, such as openings for loading microchannels of microfluidic devices, can be as small as 1 µm, but in general these capillary openings are in the range of about 10 to about 100 µm. In the context of delivery to a mass analyzer in electrospray-type mass spectrometry, the inner diameter of capillaries may range from about 0.1 to about 3 mm and preferably from about 0.5 to about 1 mm. In some instances, a capillary can represent a portion of a microfluidic device. In such instances, the capillary may be an integral or affixed (permanently or detachably) portion of the microfluidic device.

The term "fluid" as used herein refers to matter that is nonsolid, or at least partially gaseous and/or liquid, but not entirely gaseous. A fluid may contain a solid that is minimally, partially, or fully solvated, dispersed, or suspended. Examples of fluids include, without limitation, aqueous liquids (including water per se and salt water) and nonaqueous liquids such as organic solvents and the like. As used herein, the term "fluid" is not synonymous with the term "ink" in that an ink must contain a colorant and may not be gaseous.

The terms "focusing means" and "acoustic focusing means" refer to a means for causing acoustic waves to converge at a focal point, either by a device separate from the acoustic energy source that acts like an optical lens, or by the spatial arrangement of acoustic energy sources to effect convergence of acoustic energy at a focal point by constructive and destructive interference. A focusing means may be as simple as a solid member having a curved surface, or it may include complex structures such as those found in Fresnel lenses, which employ diffraction in order to direct acoustic radiation. Suitable focusing means also include phased array methods as are known in the art and described, for example, in U.S. Pat. No. 5,798,779 to Nakayasu et al. and by Amemiya et al. (1997) *Proceedings of the 1997 IS&T NIP13 International Conference on Digital Printing Technologies*, pp. 698-702. Additional information regarding acoustic focusing is provided in U.S. patent application Ser. No. 10/066,546, entitled "Acoustic Sample Introduction for Analysis and/or Processing," filed Jan. 30, 2002, inventors Ellson and Mutz.

The terms "library" and "combinatorial library" are used interchangeably herein to refer to a plurality of chemical or biological moieties arranged in a pattern or an array such that the moieties are individually addressable. In some instances, the plurality of chemical or biological moieties is present on the surface of a substrate, and in other instances the plurality of moieties represents the contents of a plurality of reservoirs. Preferably, but not necessarily, each moiety is different from each of the other moieties. The moieties may be, for example, peptidic molecules and/or oligonucleotides.

The "limiting dimension" of an opening refers herein to the theoretical maximum diameter of a sphere that can pass through an opening without deformation. For example, the limiting dimension of a circular opening is the diameter of the opening. As another example, the limiting dimension of a rectangular opening is the length of the shorter side of the rectangular opening. The opening may be present on any solid body including, but not limited to, sample vessels, substrates, capillaries, microfluidic devices, and ionization chambers. Depending on the purpose of the opening, the opening may represent an inlet and/or an outlet.

The term "moiety" refers to any particular composition of matter, e.g., a molecular fragment, an intact molecule (including a monomeric molecule, an oligomeric molecule, or a polymer), or a mixture of materials (for example, an alloy or a laminate).

The term "near," when used to refer to the distance from the focal point of the focused acoustic radiation to the surface of the fluid from which a droplet is to be ejected, indicates that the distance should be such that the focused acoustic radiation directed into the fluid results in droplet ejection from the fluid surface; one of ordinary skill in the art will be able to select an appropriate distance for any given fluid using straightforward and routine experimentation. Generally, however, a suitable distance between the focal point of the acoustic radiation and the fluid surface is in the range of about 1 to about 15 times the wavelength of the speed of sound in the fluid, more typically in the range of about 1 to about 10 times that wavelength, preferably in the range of about 1 to about 5 times that wavelength.

"Optional" or "optionally" means that the subsequently described circumstance may or may not occur, so that the description includes instances where the circumstance occurs and instances where it does not.

The term "radiation" is used in its ordinary sense and refers to emission and propagation of energy in the form of a waveform disturbance traveling through a medium such that energy is transferred from one particle of the medium to another, generally without causing any permanent displacement of the medium itself. Thus, radiation may refer, for example, to electromagnetic waveforms as well as acoustic vibrations.

Accordingly, the terms "acoustic radiation" and "acoustic energy" are used interchangeably herein and refer to the emission and propagation of energy in the form of sound waves. As with other waveforms, acoustic radiation may be focused using a focusing means, as discussed below. Although acoustic radiation may have a single frequency and associated wavelength, acoustic radiation may take a form, e.g. a linear chirp, that includes a plurality of frequencies. Thus, the term "characteristic wavelength" is used to describe the mean wavelength of acoustic radiation having a plurality of frequencies.

The term "reservoir" as used herein refers to a receptacle or chamber for containing a fluid. In some instances, a fluid contained in a reservoir will have a free surface, e.g., a surface that allows acoustic radiation to be reflected therefrom or a surface from which a droplet may be acoustically ejected. A reservoir may also be a locus on a substrate surface within which a fluid is constrained.

The term "substrate" as used herein refers to any material having a surface onto which one or more fluids may be deposited. The substrate may be constructed in any of a number of forms including, for example, wafers, slides, well plates, or membranes. In addition, the substrate may be porous or nonporous as required for deposition of a particular fluid. Suitable substrate materials include, but are not limited to, supports that are typically used for solid phase chemical synthesis, such as polymeric materials (e.g., polystyrene, polyvinyl acetate, polyvinyl chloride, polyvinyl pyrrolidone, polyacrylonitrile, polyacrylamide, polymethyl methacrylate, polytetrafluoroethylene, polyethylene, polypropylene, polyvinylidene fluoride, polycarbonate, and divinylbenzene styrene-based polymers), agarose (e.g., Sepharose®), dextran (e.g., Sephadex®), cellulosic polymers and other polysaccharides, silica and silica-based materials, glass (particularly controlled pore glass, or "CPG") and functionalized glasses, ceramics, and such substrates treated with surface coatings, e.g., with microporous polymers (particularly cellulosic polymers such as nitrocellulose), microporous metallic compounds (particularly microporous aluminum), antibody-binding proteins (available from Pierce Chemical Co., Rockford Ill.), bisphenol A polycarbonate, or the like. Additional information relating to the term "substrate" can be found in U.S. Patent Application Publication No. 200200377579 to Ellson et al.

The term "substantially" as in, for example, the phrase "substantially deviate from a predetermined volume," refers to a volume that does not deviate by more than about 25%, preferably 10%, more preferably 5%, and most preferably at most 2%, from the predetermined volume. Other uses of the term "substantially" involve an analogous definition.

The term "sample vessel" as used herein refers to any hollow or concave receptacle having a structure that allows for sample processing and/or analysis. Thus, a sample vessel has an inlet opening through which sample may be introduced and an optional, but preferred, outlet opening through which processed or analyzed sample may exit.

The invention may be employed with any type of fluid dispenser that serves to dispense one or more droplets of fluid from a reservoir. Any fluid droplet dispensing techniques known in the art may be used in conjunction with the present invention. For example, the invention may be used with dispensers such as inkjet printheads (both thermal and piezoelectric), pipettes, capillaries, syringes, displacement pumps, rotary pumps, peristaltic pumps, vacuum devices, flexible or rigid tubing, valves, manifolds, pressurized gas canisters, and combinations thereof. While nonacoustic techniques may be used to dispense fluid from the reservoir, the invention is particularly suited for use with nozzle less acoustic ejection techniques that employ focused acoustic radiation generated by acoustic ejectors, such as those described in U.S. Patent Application Publication No. 20020037579 to Ellson et al. This publication sets forth that an ejector may be acoustically coupled to a reservoir containing a fluid in order to eject a droplet therefrom. In some instances, the reservoir may be a well of a well plate. Since this device configuration allows droplets to be ejected from near the base of a well, uncontrolled electrostatic charge anywhere in the well, e.g., the base or sidewalls, may have a strong effect influence on the volume and/or trajectory of such droplets.

Since acoustic ejection provides a number of advantages over other fluid dispensing technologies, some embodiments of the invention employ a device for acoustically ejecting a droplet of fluid from a reservoir. The device is comprised of a reservoir adapted to contain a fluid, an ejector for ejecting a droplet from the reservoir, and a means for positioning the ejector in acoustic coupling relationship to the reservoir. The ejector comprises an acoustic radiation generator for generating acoustic radiation and a focusing means for focusing the acoustic radiation generated by the generator. As described in U.S. Patent Application Publication No. 20020037579 to Ellson et al., the acoustic radiation is focused at a focal point within and sufficiently near the fluid surface in the reservoir to result in the ejection of droplets therefrom. Furthermore, a means is provided for reducing any uncontrolled electrostatic charge on the device or a portion thereof that alters the volume and/or trajectory of a droplet ejected from the reservoir. As a result, the volume and/or trajectory of the ejected droplet do not substantially deviate from a predetermined volume and/or predetermined trajectory.

The device may be constructed to include the reservoir as an integrated or permanently attached component of the device. However, to provide modularity and interchangeability of components, it is preferred that the device be constructed with a removable reservoir. Optionally, a plurality of reservoirs many be provided. Generally, the reservoirs are arranged in a pattern or an array to provide each reservoir with individual systematic addressability. In addition, while each of the reservoirs may be provided as a discrete or stand-alone item, in circumstances that require a large number of reservoirs, it is preferred that the reservoirs be attached to each other or represent integrated portions of a single reservoir unit. For example, the reservoirs may represent individual wells in a well plate.

Many well plates suitable for use with the device are commercially available and may contain, for example, 96, 384, 1536, or 3456 wells per well plate, having a full skirt, half skirt, or no skirt. The wells of such well plates typically form rectilinear arrays. Manufacturers of suitable well plates for use in the employed device include Corning, Inc. (Corning, N.Y.) and Greiner America, Inc. (Lake Mary, Fla.). However, the availability of such commercially available well plates does not preclude the manufacture and use of custom-made well plates containing at least about 10,000 wells, or as many as 100,000 to 500,000 wells, or more. The wells of such custom-made well plates may form rectilinear or other types of arrays. As well plates have become commonly used laboratory items, the Society for Biomolecular Screening (Danbury, Conn.) has formed the Microplate Standards Development Committee to recommend and maintain standards to facilitate the automated processing of small volume well plates on behalf of and for acceptance by the American National Standards Institute.

Furthermore, the material used in the construction of reservoirs must be compatible with the fluids contained therein. Thus, if it is intended that the reservoirs or wells contain an organic solvent such as acetonitrile, polymers that dissolve or swell in acetonitrile would be unsuitable for use in forming the reservoirs or well plates. Similarly, reservoirs or wells intended to contain DMSO must be compatible with DMSO. For water-based fluids, a number of materials are suitable for the construction of reservoirs and include, but are not limited to, ceramics such as silicon oxide and aluminum oxide, metals such as stainless steel and platinum, and polymers such as polyester and polytetrafluoroethylene. For fluids that are photosensitive, the reservoirs may be constructed from an optically opaque material that has sufficient acoustic transparency for substantially unimpaired functioning of the device. Thus, the reservoir may be adapted to contain any type of fluid, metallic or nonmetallic, organic or inorganic.

When a plurality of reservoirs is employed, the acoustic radiation generator may have to be aligned with each reservoir during operation, discussed infra. In order to reduce the amount of movement and time needed to align the generator successively with each reservoir, it is preferable that the center of each reservoir be located not more than about 1 centimeter, more preferably not more than about 1.5 millimeters, still more preferably not more than about 1 millimeter and optimally not more than about 0.5 millimeter, from a neighboring reservoir center. These dimensions tend to limit the size of the reservoirs to a maximum volume. The reservoirs are constructed to contain typically no more than about 1 mL, preferably no more than about 100 µL, more preferably no more than about 10 µL, still more preferably no more than about 1 µL, and optimally no more than about 1 nL, of fluid. The reservoirs may be either completely or partially filled with fluid. For example, fluid may occupy a volume of about 10 pL to about 100 nL.

When an array of reservoirs is provided, each reservoir may be individually, efficiently, and systematically addressed. Although any type of array may be employed, arrays comprised of parallel rows of evenly spaced reservoirs are preferred. Typically, though not necessarily, each row contains the same number of reservoirs. Optimally, rectilinear arrays comprising X rows and Y columns of reservoirs are employed with the invention, wherein X and Y are each at least 2. In some instances, X may be greater than, equal to, or less than Y. In addition, nonrectilinear arrays as well as other geometries may be employed. For example, hexagonal, spiral, or other types of arrays may be used. In some instances, the invention may be employed with irregular patterns of reservoirs, e.g., droplets randomly located on a flat substrate surface. In addition, the invention may be used with reservoirs associated with microfluidic devices.

Moreover, the invention may be used to transport fluids of virtually any type and amount desired. The fluid may be aqueous and/or nonaqueous. Examples of fluids include, but are not limited to, aqueous fluids including water per se and water-solvated ionic and non-ionic solutions; organic solvents; lipidic liquids; suspensions of immiscible fluids; and suspensions or slurries of solids in liquids. Because the invention is readily adapted for use with high temperatures, fluids such as liquid metals, ceramic materials, and glasses may be used, as described in U.S. Patent Application Publication No. 20020140118. In some instances, the reservoir may contain a biomolecule, nucleotidic, peptidic, or otherwise. In addition, the invention may be used in conjunction with dispensers for dispensing droplets of immiscible fluids, as described in U.S. Patent Application Publication Nos. 2002037375 and 20020155231, or to dispense droplets containing pharmaceutical agents, as discussed in U.S. Patent Application Publication No. 20020142049 and U.S. patent application Ser. No. 10/244,128, entitled "Precipitation of Solid Particles from Droplets Formed Using Focused Acoustic Energy," filed, Sep. 13, 2002, inventors Lee, Ellson and Williams.

Any of a variety of focusing means may be employed to focus acoustic radiation so as to eject droplets from a reservoir. For example, one or more curved surfaces may be used to direct acoustic radiation to a focal point near a fluid surface. One such technique is described in U.S. Pat. No. 4,308,547 to Lovelady et al. Focusing means with a curved surface have been incorporated into the construction of commercially available acoustic transducers such as those manufactured by Panametrics Inc. (Waltham, Mass.). In addition, Fresnel lenses are known in the art for directing acoustic energy at a predetermined focal distance from an object plane. See, e.g., U.S. Pat. No. 5,041,849 to Quate et al. Fresnel lenses may have a radial phase profile that diffracts a substantial portion of acoustic energy into a predetermined diffraction order at diffraction angles that vary radially with respect to the lens. The diffraction angles should be selected to focus the acoustic energy within the diffraction order on a desired object plane. It should be noted that acoustic focusing means exhibiting a variety of F-numbers may be employed with the invention. As discussed in U.S. Pat. No. 6,416,164 to Stearns et al., however, low F-number focusing places restrictions on the reservoir and fluid level geometry and provides relatively limited depth of focus, increasing the sensitivity to the fluid level in the reservoir. Thus, the focusing means suitable for use with the invention typically exhibits an F-number of at least about 1. Preferably, the focusing means exhibits an F-number of at least about 2.

There are a number of ways to acoustically couple the ejector to a reservoir and thus to the fluid therein. One such approach is through direct contact, as is described, for example, in U.S. Pat. No. 4,308,547 to Lovelady et al., wherein a focusing means constructed from a hemispherical crystal having segmented electrodes is submerged in a liquid to be ejected. The aforementioned patent further discloses that the focusing means may be positioned at or below the surface of the liquid. However, this approach for acoustically coupling the focusing means to a fluid is undesirable when the ejector is used to eject different fluids in a plurality of containers or reservoirs, as repeated cleaning of the focusing means would be required in order to avoid cross-contamination. The cleaning process would necessarily lengthen the transition time between each droplet ejection event. In addition, in such a method, fluid would adhere to the ejector as it is removed from each container, wasting material that may be costly or rare.

Thus, a preferred approach is to acoustically couple the ejector to the reservoir without contacting any portion of the ejector, e.g., the focusing means, with the fluids to be ejected. When a plurality of reservoirs is employed, a positioning means is provided for positioning the ejector in controlled and repeatable acoustic coupling with each of the fluids in the reservoirs to eject droplets therefrom without submerging the ejector therein. This typically involves direct or indirect contact between the ejector and the external surface of each reservoir. When direct contact is used in order to acoustically couple the ejector to each reservoir, it is preferred that the direct contact be wholly conformal to ensure efficient acoustic energy transfer. That is, the ejector and the reservoir should have corresponding surfaces adapted for mating contact. Thus, if acoustic coupling is achieved between the ejector and reservoir through the focusing means, it is desirable for the reservoir to have an outside surface that corresponds to the surface profile of the focusing means. Without conformal contact, efficiency and accuracy of acoustic energy transfer may be compromised. In addition, since many focusing means have a curved surface, the direct contact approach may necessitate the use of reservoirs having a specially formed inverse surface.

When an ejector is placed in indirect contact with a reservoir, an acoustic coupling medium may be interposed between the reservoir and ejector. Typically, the acoustic coupling medium is a fluid. In addition, the acoustic coupling medium is preferably an acoustically homogeneous material that is substantially free of material having different acoustic properties than the fluid medium itself. Furthermore, it is preferred that the acoustic coupling medium be comprised of a material having acoustic properties that facilitate the transmission of acoustic radiation without significant attenuation in acoustic pressure and intensity. Also, the acoustic impedance of the coupling medium should facilitate the transfer of energy from the coupling medium into the reservoir. An aqueous fluid, such as water per se, may be employed as an acoustic coupling medium. Ionic additives, e.g., salts, may sometimes be added to the coupling medium to increase the conductivity of the coupling medium.

A single ejector is preferred, although an acoustic ejection system may include a plurality of ejectors. When a single ejector is employed, the means for positioning the ejector may be adapted to provide relative motion between the ejector and reservoirs. The positioning means should allow for the ejector to move from one reservoir to another quickly and in a controlled manner, thereby allowing fast and controlled scanning of the reservoirs to effect droplet ejection therefrom. Thus, various means for positioning the ejector in acoustic coupling relationship to the reservoir are generally known in the art and may involve, e.g., devices that provide movement having one, two, three, four, five, six, or more degrees of freedom. Accordingly, when rows of reservoirs are provided, relative motion between the acoustic radiation generator and the reservoirs may result in displacement of the acoustic radiation generator in a direction along the rows. Similarly, when a rectilinear array of reservoirs is provided, the ejector may be movable in a row-wise direction and/or in a direction perpendicular to both the rows and columns.

Current positioning technology allows for the ejector positioning means to move from one reservoir to another quickly and in a controlled manner, thereby allowing fast and controlled ejection of different fluid samples. That is, current commercially available technology allows the ejector to be moved from one reservoir to another, with repeatable and controlled acoustic coupling at each reservoir, in less than about 0.1 second for high performance positioning means and in less than about 1 second for ordinary positioning means. A custom designed system will allow the ejector to be moved from one reservoir to another with repeatable and controlled acoustic coupling in less than about 0.001 second.

Acoustic ejection also enables rapid ejection of droplets from one or more reservoirs, e.g., at a rate of at least about 1,000,000 droplets per minute from the same reservoir, and at a rate of at least about 100,000 drops per minute from different reservoirs, assuming that the droplet size does not exceed about 10 µm in diameter. One of ordinary skill in the art will recognize that the droplet generation rate is a function of drop size, viscosity, surface tension, and other fluid properties. In general, the droplet generation rate increases with decreasing droplet diameter, and 1,000,000 droplets per minute is achievable for most aqueous fluid drops under about 10 µm in diameter.

Acoustic ejection may be used in any context where precise placement of a fluid droplet is desirable or necessary. In particular, the invention may be employed to improve accuracy and precision associated with nozzleless acoustic ejection. For example, it is described in U.S. Patent Application Publication No. 20020037579 to Ellson et al. that acoustic ejection technology may be used to form biomolecular arrays. Similarly, acoustic ejection technology may be employed to format a plurality of fluids, e.g., to transfer fluids from odd-sized bulk containers to wells of a standardized well plate or to transfer fluids from one well plate to another. Furthermore, as described in U.S. Patent Application Publication Nos. 20020109084 and 20020125424, each to Ellson et al., focused acoustic radiation may serve to eject a droplet of fluid from a reservoir into any sample vessel for processing and/or analyzing a sample molecule, e.g., into a sample introduction interface of a mass spectrometer, an inlet opening that provides access to the interior region of a capillary, or an inlet port of a microfluidic device. Similarly, the invention may be used to transport droplets of analysis-enhancing fluid on a sample surface in order to prepare the sample for analysis, e.g., for MALDI or SELDI-type analysis.

In order to prepare an array on a substrate surface, the substrate must be placed in droplet-receiving relationship to a reservoir. Thus, the invention may also employ a positioning means for positioning the substrate. With respect to the substrate positioning means and the ejector positioning means, it is important to keep in mind that there are two basic kinds of motion: pulse and continuous. For the ejector positioning means, pulse motion involves the discrete steps of moving an ejector into position, emitting acoustic energy, and moving the ejector to the next position; again, using a high performance positioning means with such a method allows repeatable and controlled acoustic coupling at each reservoir in less than 0.1 second. A continuous motion design, on the other hand, moves the ejector and the reservoirs continuously, although not necessarily at the same speed, and provides for ejection during movement. Since the pulse width is very short, this type of process enables over 10 Hz reservoir transitions, and even over 1000 Hz reservoir transitions. Similar engineering considerations are applicable to the substrate positioning means.

From the above, it is evident that the relative positions and spatial orientations of the various components may be altered depending on the particular desired task at hand. In such a case, the various components of the device may require individual control or synchronization to direct droplets onto designated sites on a substrate surface. For example, the ejector positioning means may be adapted to eject droplets from each reservoir in a predetermined sequence associated with an array of designated sites on the substrate surface. Any positioning means of the present invention may be constructed from, e.g., levers, pulleys, gears, a combination thereof, or other mechanical means known to one of ordinary skill in the art.

FIG. 1 illustrates an exemplary focused acoustic ejection device suitable for use with the invention, in simplified cross-sectional view. As with all figures referenced herein, in which like parts are referenced by like numerals, FIG. 1 is not to scale, and certain dimensions may be exaggerated for clarity of presentation. The device 11 includes a plurality of reservoirs, i.e., at least two reservoirs—a first reservoir indicated at 13 and a second reservoir indicated at 15. Each reservoir contains a combination of two or more immiscible fluids, and the individual fluids as well as the fluid combinations in the different reservoirs may be the same or different. As shown, reservoir 13 contains fluid 14, and reservoir 15 contains fluid 16. Fluids 14 and 16 have fluid surfaces respectively indicated at 17 and 19. As shown, the reservoirs are of substantially identical construction so as to be substantially acoustically indistinguishable, but identical construction is not a requirement. The reservoirs are shown as separate removable components but may, if desired, be fixed within a plate or other substrate. Each of the reservoirs 13 and 15 is axially, symmetric as shown, having vertical walls 21 and 23 extending upward from circular reservoir bases 25 and 27 and terminating at openings 29 and 31, respectively, although other reservoir shapes may be used. The material and thickness of each reservoir base should be such that acoustic radiation may be transmitted therethrough and into the fluid contained within the reservoirs.

The device also includes an acoustic ejector 33 comprised of an acoustic radiation generator 35 for generating acoustic radiation, and a focusing means 37 for focusing the acoustic radiation at a focal point near the fluid surface from which a droplet is to be ejected, wherein the focal point is selected so as to result in droplet ejection. The focal point may be in the upper fluid layer or the lower fluid layer, but is preferably just below the interface therebetween. As shown in FIG. 1, the focusing means 37 may comprise a single solid piece having a concave surface 39 for focusing acoustic radiation, but the focusing means may be constructed in other ways as discussed below. The acoustic ejector 33 is thus adapted to generate and focus acoustic radiation so as to eject a droplet of fluid from each of the fluid surfaces 17 and 19 when acoustically coupled to reservoirs 13 and 15, respectively. The acoustic radiation generator 35 and the focusing means 37 may function as a single unit controlled by a single controller, or they may be independently controlled, depending on the desired performance of the device. Typically, single ejector designs are preferred over multiple ejector designs, because accuracy of droplet placement, as well as consistency in droplet size and velocity, are more easily achieved with a single ejector.

In operation, each reservoir 13 and 15 of the device is filled with different fluids, as explained above. The acoustic ejector 33 is positionable by means of ejector positioning means 43, shown below reservoir 13, in order to achieve acoustic coupling between the ejector and the reservoir through acoustic coupling medium 41. If droplet ejection onto a substrate is desired, a substrate 49 may be positioned above and in proximity to the first reservoir 13 such that one surface of the substrate, shown in FIG. 1 as underside surface 51, faces the reservoir and is substantially parallel to the surface 17 of the fluid 14 therein. The substrate 49 is held by substrate positioning means 53, which, as shown, is grounded. Thus, when the substrate 49 is comprised of a conductive material, the substrate 49 is grounded as well. Once the ejector, the reservoir, and the substrate are in proper alignment, the acoustic radiation generator 35 is activated to produce acoustic radiation that is directed by the focusing means 37 to a focal point 55 near the fluid surface 17 of the first reservoir. As a result, droplet 57 is ejected from the fluid surface 17, optionally onto a particular site (typically although not necessarily, a pre-selected, or "predetermined" site) on the underside surface 49 of the substrate. The ejected droplet may be retained on the substrate surface by solidifying thereon after contact; in such an embodiment, it is necessary to maintain the substrate surface at a low temperature, i.e., at a temperature that results in droplet solidification after contact. Alternatively, or in addition, a molecular moiety within the droplet attaches to the substrate surface after contact, through adsorption, physical immobilization, or covalent binding.

Figure 1B:
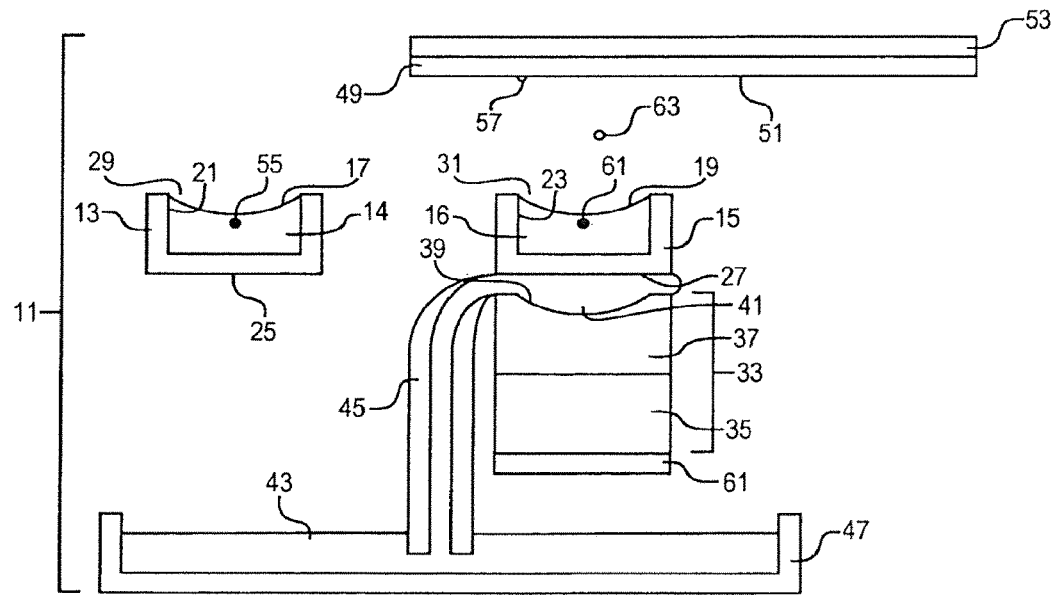

Then, as shown in FIG. 18, a substrate positioning means 53 may be used to reposition the substrate 49 (if used) over reservoir 15 in order to receive a droplet therefrom at a second site. FIG. 1B also shows that the ejector 33 has been repositioned by the ejector positioning means 59 below reservoir 15 and in acoustically coupled relationship thereto by virtue of acoustic coupling medium 41. Once properly aligned, as shown in FIG. 1B, the acoustic radiation generator 35 of ejector 33 is activated to produce acoustic radiation that is then directed by focusing means 37 to a focal point within the reservoir fluids in reservoir 15, thereby ejecting droplet 63, optionally onto the substrate.

It should be evident that such operation is illustrative of how an acoustic ejector may be used to eject a plurality of droplets from reservoirs in order to form a pattern, e.g., an array, on the substrate surface 51. It should be similarly evident that an acoustic ejector may be adapted to eject a plurality of droplets from one or more reservoirs onto the same site of the substrate surface. Furthermore, the ejection of a plurality of droplets may involve one or more ejectors. In some instances, the droplets are ejected successively from one or more reservoirs. In other instances, droplets are ejected simultaneously from different reservoirs.

Figure 2:
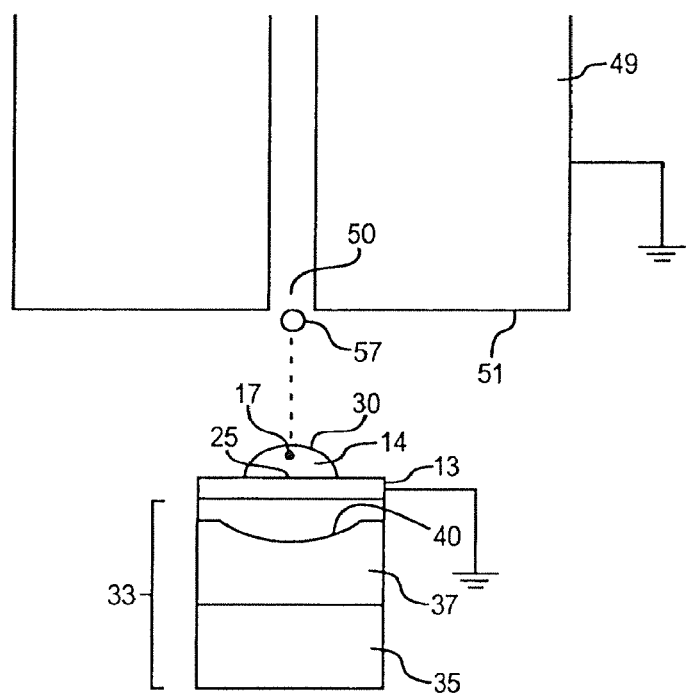
FIG. 2 illustrates in cross-sectional schematic view the ejection of droplets of fluid from a volume of fluid on a substrate surface into an inlet opening disposed on a terminus of a capillary.

As depicted in FIG. 2, the invention may be used with a single reservoir to transport fluid into an inlet opening of a target vessel. Axially symmetric capillary 49 having an inlet opening 50 disposed on a terminus 51 thereof is provided as a target vessel. Due to the axial symmetry of the capillary 49, the inlet opening 50 has a circular cross section. As such, the opening has a limiting dimension equal to its diameter.

A hemispherical volume of fluid 14 on a substantially flat surface 25 of a substrate 13 serves a reservoir. The shape of fluid 14 is a function of the sample wetting properties with respect to the substrate surface 25. Thus, the shape can be modified with any of a number of surface modification techniques. In addition, an ejector 33 is provided comprising an acoustic radiation generator 35 for generating radiation, and a focusing means 37 for directing the radiation at a focal point near the surface 17 of the fluid 14. The ejector 33 is shown in acoustic coupling relationship to the substrate 13 through coupling fluid 41. Proper control of acoustic wavelength and amplitude results in the ejection of a droplet 57 from the fluid 14 on the substrate 13. As the droplet 57 is shown having a diameter only slightly smaller than the diameter of the inlet opening 49, it is evident that this configuration requires strict control over the droplet size and trajectory.

The invention is in general a system or method for fluid transport. A quantity of fluid is held in a reservoir. A droplet generator is employed to generate droplets from the fluid, for example a nozzle-based system or a nozzleless system such as an acoustic ejection system. The droplet generator may or may not make contact with the fluid in order to generate the droplet. The droplet generator may be set up to move from one reservoir to another in order to be able to eject from more than one reservoir. In a common arrangement, a number of reservoirs form part of an integral structure, e.g., a well plate, and the structure is moved by suitable mechanical or electromechanical systems, potentially under computer control, into a suitable position with respect to the droplet generator.

The droplet generator is controlled by a controller, preferably electronic and connectable to computers through some communications system. The droplets after generation arrive at a target, which may be for example a well plate, a porous or non-porous surface, a substrate, or a structure which is to be coated by the droplets. The invention also includes a circuit which controls a characteristic of the generated droplet, increasing the likelihood that the droplet will not splash or bounce on arriving at the target. This circuit may be controlled by the controller or may form part of the controller. The target may already have a quantity of fluid, and the droplet may coalesce with that quantity of fluid.

In general the invention may be used with a range of fluids and targets. For example, a fluid in the target with which coalescence could be desired to occur may be of different composition from the fluid in the droplet. A common compositional difference encountered in practice is ratio of DMSO to water where solutions comprising mixtures of DMSO and water are transported. Compositional differences may lead to differences in physical parameters such as viscosity and dielectric constant. Thus, for example, a 70% DMSO/30% water mixture has a viscosity of roughly 3.5 centipoise while an aqueous buffer would have a viscosity of roughly 1 centipoise. Thus the droplets of the invention may have a viscosity which is more than 3 times that of the fluid at the target, or vice versa.

The fluid with which coalescence could be desired to occur may be of approximately the same volume as the droplet, for example another droplet of similar size or two droplets of similar size, or it may be a larger quantity of fluid, for example a quantity of fluid more than 100 times larger than the droplet.

A preferred controller contains a microprocessor with suitable memory and software or firmware. The microprocessor may be running an operating system specialized for real time and embedded applications, as for example QNX from QNX Software Systems (Ottawa, Ontario, Canada). Some controllers may contain two or more microprocessors and distribute functions among them as is convenient from the point of view of the design and operation of the system. Such a controller is preferably connected to a display allowing direct operator interaction with the fluid transport system by pressing of buttons or through a touch screen. Such a controller is also preferably provided with communications software, firmware and/or hardware which allows it to communicate with computers including general-purpose computers which can form part of an overall laboratory or manufacturing automation network, and which would allow the controller to operate the fluid transport system in an automated manner based on commands or information received from other entities in the overall laboratory or manufacturing automation system.

An overall laboratory automation system may include, for example, a carousel for holding well plates, a robot arm for moving well plates from one instrument to another, a variety of analytical instruments and reaction chambers, a pin based fluid transfer system, and/or an acoustic ejection system. The overall purposes of the system may include taking quantities of fluids and subjecting them to analyses (including for example the ascertainment of their composition and physical properties), reactions designed to produce particular moieties, and purification steps, all the while potentially keeping track, by computerized or other means, of the origin and destination of each fluid in the system and of the processes and results for each fluid. The system may also be employed to generate for further use objects which contain or are coated with fluids moved by the system.

The tracking of the origin, destination, processes, and results for each fluid may be performed, for example, by having controllers such as the fluid transport system controller communicate that information to a general purpose computer which stores the information as flat files or in a database. Fluids are conveniently identified by assigning an identifier to each well plate in the system and by tracking what is done to each well in each plate at particular times in a way that allows one to produce an overall history for the contents of each well of each plate. It must be kept in mind in this regard that not all changes in fluids in the system take place as a result of deliberate or planned action; some may be inevitable changes that occur as a result of the passage of time, as for example the absorption of water from the surrounding air or the evaporation of fluids in storage.

In a laboratory automation system it will generally be necessary to integrate equipment from different manufacturers. In this connection the adherence to particular standards may be a desirable feature of a fluid transport system. Certain fluid transport systems which form part of a manufacturing environment may be required to meet further standards relating to manufacturing as well as being able to support overall system conformance with the norms of "Good Manufacturing Practice" (GMP) as understood by the pharmaceutical industry. In particular applications the fluids being transported may be pathogenic requiring special measures for their handling which may impact on the design of the controller.

A preferred controller of a fluid transport system will also optionally contain detailed information for achieving efficient transport of fluid within the system. Such information might be, for example, preferred ranges of droplet speeds as discussed below, preferred ranges of Weber numbers, and physical characteristics of the fluids being manipulated, as for example their conductivity and permittivity, which are also discussed below, and also their density, viscosity, surface tension, and the like. Such information will also include algorithms for operating in a suitably time-sequenced manner the different actuators of the fluid transport system, for example well plate transport systems, pin based fluid transport systems, robot arms, acoustic ejector transducers, and the electrodes discussed in connection with certain embodiments below. The time-sequenced algorithms may be stored in the form of tables which are interpreted by suitable software or firmware or they may be coded directly as programs or they may be a mixture of tables and code. The time-sequenced algorithms may take into account information obtained from various sensors in the system, for example position and temperature sensors and digital cameras, as well as stored or measured characteristics of the fluids being manipulated. Preferably the algorithms may be modified in the field, e.g., by software downloads over a network, to take into account the most recent knowledge about the best known methods for the operation of the fluid transport system. The controller may also have learning capabilities in which it can, through analysis of fluids, determine by itself some of the parameters most suitable for their efficient transport.

One way to control characteristics of the droplets in a fluid transport system to reduce the likelihood of splashing or bounce is to control the speed with which the droplet approaches the target. The manner in which the speed control is accomplished may depend on the droplet generation technique.

Gravity and friction against the surrounding air or other gas have an impact on droplet speed which has been studied in connection with the modeling of the behavior of raindrops. Some control of the impact of these forces is possible, particularly in the case of downward flow where the drop height can influence the speed of the droplet at impact. Because it is difficult to zero out the effect of these forces, their effect may need to be taken into account in designing systems even where the primary control of droplet speed is achieved by other means. The system of the invention encompasses and contemplates the possibility that the droplet will travel, upon being generated, in a direction generally against the force of the earth's gravitational attraction, in particular in a direction 90 to 180 degrees with respect to the vector which gives the direction of the earth's gravitational attraction.

Nanoliter scale droplets of water-like properties have been studied. For such droplets it is found that speeds which are preferable for droplet approach with coalescence are in the range of 0.2 to 10 m/s. A more preferable range is 1.0 to 2.5 m/s, and within that range a value above 1.5 m/s is particularly preferred.

Electric fields may have an impact on the speed of a droplet, as discussed for example in U.S. Pat. No. 5,541,627 to Quate, which states generally that water is attracted to an electric field. This impact may exist even if the droplet is uncharged if the electric field causes the droplet to become electrically polarized, as will occur if the droplet consists primarily of a polarizable solvent such as water.

It is believed that an uncharged drop will only feel a net force on it in a nonuniform electric field. In any field, the drop will develop an induced dipole charge, i.e. a separation of charges, just as is the case for any dielectric. A dipole in turn will be attracted toward a concentration of electric field, that is toward a region of greater field. In a uniform field, the dipole experiences no net force. Mathematically, the force is proportional to the gradient of the square of the external electric field.

When an acoustic ejection system is used for droplet generation, it is found that the speed of the droplet is controllable within a range through the amount of acoustic energy used to cause the ejection to occur. It has been found, for example, that for 5 nL droplets of 70% DMSO/30% water in an acoustic ejection system using an F2 lens, control of the speed between 0.5 and 3 m/s may be achieved readily through control of acoustic energy above ejection threshold.

An alternative way to control characteristics of the droplet to reduce the likelihood of splashing or bounce is to control the Weber number of the impact. The Weber number is a dimensionless quantity intended to express the ratio of inertia force to surface tension force. It is defined as $\rho V^2 l/\sigma$ where $\rho$ is the density of the fluid, V is the velocity, l is a characteristic length, and $\sigma$ is surface tension. For a droplet impact l may be taken to be droplet diameter. Of these parameters, it may be easier to control V and l. In the literature there are indications that particular ranges of Weber numbers are associated with coalescence, at least with the fluids studied in the particular literature references. Because of this, it may be desirable for the improvement of coalescence and control of splashing and bounce to control the parameters that make up the Weber number of a droplet in order to confine that Weber number within particular ranges. The particular ranges may vary according to the composition of the droplets and of the fluid into which the droplets are intended to merge. The parameters that are controlled may include the velocity V and the characteristic length l. The characteristic length l may be controlled, for example, by using two smaller droplets in place of one larger one, if that would improve coalescence properties:

A further preferred way to control characteristics of the droplet is to generate an electric field in a zone of space through which the droplet passes. Preferably such an electric field is generated in the zone of space in which the droplet is generated.

An electric field in a zone through which the droplet passes may be directed with different orientations. It is preferred that the electric field be oriented along the direction of droplet separation from a larger mass of fluid.

An electric field in a zone through which the droplet passes may be of different magnitudes. For nanoliter scale droplets, it is preferred that the electric field lie between 1,000 and 100,000 V/m, preferably between 10,000 and 100,000 V/m, more preferably between 25,000 and 50,000 V/m, and most preferably between 30,000 and 40,000 V/m. To the extent the field is non-uniform, it is preferred that the field in the zone of space in which the droplet is generated lie within the preferential ranges just discussed. The desired intensity of the electric field would preferably be increased relative to these values if the fluid of the droplet is only modestly conductive, for example much less conductive than pure water.

It is believed that an electric field component in the direction of droplet separation from a larger mass of fluid may cause the droplet to have an electric charge when it is separated, and that the existence of such electric charges can, if they are of appropriate magnitudes, facilitate droplet coalescence. The mechanism of facilitation is not clearly understood, but it is believed to be an effect above and beyond the possible acceleration of the droplet by the electric field. A mechanism which has been hypothesized is an effective change in the droplet's surface tension with the free charge present. The surface tension is reduced because the charges on the drop surface repel one another.

With certain forms of droplet generation (e.g., acoustic ejection), droplet separation from a mass of fluid, is commonly preceded by the formation of a projection from the fluid surface. For a fluid of some degree of conductivity, in the presence of an electric field, such a projection should become charged so as to maintain it at an approximate electric equipotential with the mass of fluid. It is hypothesized that as the droplet forms from the projection, the projection is essentially pinched off, and the net charge developed along the surface of the projection is carried away with the drop. The charge on the droplet may be approximately described by the relation $Q \sim 4\pi \in_0 ahE$ where a denotes the droplet radius, h denotes the height of the mound at the time of droplet break-off, and E denotes the electric field intensity. In acoustic ejection, for DMSO/water mixtures the height h has been observed to be approximately 5 times the drop diameter, so that $h \sim 10a$. An empirical study of the charge on acoustically ejected droplets is presented as part of Example 1 below.

It is believed that an electric field component in the direction of droplet arrival at the target may assist in the coalescence on account of the polarization which the droplet will experience. In general, a dielectric in the presence of an external electric field will develop a dipole moment, corresponding to a separation of charge along the direction of the external field. This redistribution of charges counteracts the external field in such a way as to cause the net electric field strength inside the dielectric to be smaller than the external field strength, and in the limiting case of a perfectly conductive material, to be zero. In the particular case of a droplet approaching and potentially coalescing with a mass of fluid, if there is an electric field in the direction of approach, the induced dipole moment of the droplet will cause it to be attracted to the fluid mass.

Figure 3:
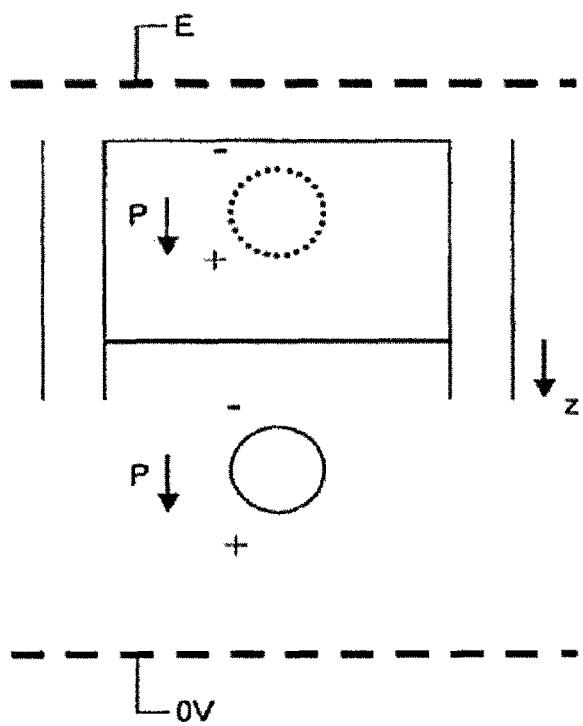
FIG. 3 depicts the approach of a droplet to a target with an electric field in the direction of droplet approach.

Two limiting cases of this occur if the fluid mass is either (1) of the same size as the approaching droplet, or (2) is much larger than the approaching droplet, so that it can be considered an infinite half-space. These cases are very similar, especially for a relatively conducting fluid, which in practice is common. For the case in which the mass of fluid is very large, the induced dipole moment of the ejected droplet can be considered to generate a mirror dipole moment within the fluid mass, consistent with the method of images well known in electrostatics, as depicted in FIG. 3. Treating the polarization of the droplet as that of a spherical conductor (a reasonable approximation for high-dielectric-constant fluids), the dipole moment of the ejected drop may be written as:

$$p = 4\pi \in_0 E a^3$$

where $\in_0$ denotes the permittivity of free space, E denotes the applied external electric field in the vicinity of the target, and a is the radius of the drop. For simplicity, we consider the geometry of FIG. 3, where z is in the (downward) vertical direction, and the target is taken to be at z=0. The z-component of the electric field due to the "image" (upper) droplet, at the position of the arriving droplet, a height z below the fluid surface, can be written as:

$$E_z = \tfrac{1}{4} E a^3 / z^3$$

It follows that the force on the arriving droplet, due to the interaction of its dipole moment with this electric field is:

$$F_z = p \, dE_z/dz = 3/2 \, \pi \in_0 E^2 a^6 / z^4$$

This force is directed upward, attracting the arriving droplet toward the surface of the fluid at the target. The force, which varies as the inverse fourth power of the height of the droplet below the fluid surface, will be strongest when the droplet is very near the surface of the receiving fluid. When the droplet just "touches" the receiving well fluid, i.e. when z=a, the dipole force is $$F_z = 3/2 \ \pi \epsilon_0 E^2 a^2$$

With an electric field of 30,000 V/m and 2.5 nl drops, the associated drop radius is 84 μm and the dipole force with z=a is approximately $F_z \sim 3 \times 10^{-10}$ N. This may be compared to the gravitational force on the drop mg~$2.6 \times 10^{-8}$ N. Thus, the dipole force is only about one hundredth that of gravity.

For the other limiting case, in which the receiving mass of fluid is of the same size as the ejected droplet, the analysis is very similar to that above. In this case, the receiving fluid mass forms a physical dipole moment equivalent to that of the drop, in the presence of the external electric field. Thus, what was previously an image dipole at a distance 2z from the ejected drop, is now an equivalent dipole, at a distance z from the drop. Hence the dipole-dipole force between the ejected drop and the receiving fluid mass is 8 times larger than that for the previous case, when the ejected drop is a distance z from the fluid mass. On the other hand, the limiting distance between the ejected drop and receiving fluid mass is now 2a. Thus the maximum force between the ejected drop and receiving fluid mass is half that described previously for the semi-infinite fluid mass. It is seen therefore that the polarization effects responsible for attraction of ejected drop to the receiving fluid mass are of the same order of magnitude, for the two limiting cases.

When using an electric field to reduce splash and bounce and/or improve droplet coalescence, it may be desirable that the electric field not substantially affect the path followed by droplet prior to its arrival at the target. It may even be desirable that the electric field not substantially alter the speed of the droplet, effecting for example a change of no more than 10% in the velocity. Such relative independence of the path and speed from electric field may be helpful, for example, in order to make it easier to ensure that successive droplets aimed at the same place on the target arrive at that place on the target repeatably. If the fluid on the target is itself being deposited droplet by droplet, as where the fluid transfer system is transferring a larger quantity of fluid as a series of droplets, such repeatability may be desirable to facilitate coalescence. Studies in the literature such as that authored by Professor Orme cited above indicate that the impact parameter has been seen as being of importance in coalescence of raindrops. The independence of path and speed from electric field may also be helpful simply in order to make other parameters of the total fluid transport system settable independently of the electric field.

A common way to generate an electric field in a region of space is to have two electrodes A and B which are held at different potentials, such that the region of space overlaps with the region between the electrodes. The electrodes may have a wide variety of shapes, for example, flat sheets of solid sufficiently conducting material, material of low conductivity coated or laminated with material of higher conductivity, rows of wires, and grids of wires. There is considerable freedom in the placement of the electrodes, for example to avoid obstructing the flow of fluid or the movement of reservoirs and targets. Alternatively, as in examples 3 and 4 below, an electrode may be placed in the path of the fluid with holes to allow the fluid to pass through.

A voltage may be permanently wired into the system and the electrodes energized at the fixed voltage whenever the system is powered on. This would make sense, for example, if a particular electrode voltage is found to be advantageous during generation of droplets in the operating range in which a fluid transfer system of the invention is expected to be used. Alternatively, and for greater flexibility, it is possible to make the voltages settable, for example, through the controller of the fluid transport system, or through one or more external inputs to the circuit producing the electric field. Under certain circumstances it can be advantageous to have a time varying voltage, for example a voltage which changes during different stages of the generation of each droplet, or a voltage which is held at a constant value for a predetermined time, for example during droplet generation, and zero otherwise.

As is discussed in detail in U.S. patent application Ser. No. 10/340,557 to Mutz et al., various phenomena exist which can cause droplets to have uncontrolled charge. It is possible to deal with uncontrolled charge in various ways which involve in general terms providing a conducting path, or providing ionization, so that the fluid from which droplets are formed discharges. For example, the reservoirs in which the fluid is held might be made from a sufficiently conducting material and grounded.

In connection with the embodiment of this invention in which the droplet characteristics are controlled by means of an electric field, it is found to be helpful to also use measures for the reduction of electric charge of the general type described in application Ser. No. 10/340,557. It is particularly helpful to have the reservoir holding fluid from which droplets are made be an approximate or exact ground, using techniques discussed in that application such as ionization discharging. In that case, a single electrode held at a nonzero voltage with respect to ground can create the electric field which is used for droplet control.

The voltages of the electrodes which are used to create the electric field can be adjusted by those of skill in the art to achieve a desired field intensity. The adjustment can be, for example, purely experimental. It can alternatively be based on well known formulas (e.g., for the electric field between parallel plates) as found for example in books on electromagnetics such as J. D. Jackson, *Classical Electrodynamics* (2d ed. 1975). It can alternatively be based on well known numerical techniques for computing electrostatic fields by numerical solution of Laplace's equation.

Alternatively, the voltages of the electrodes may be adjusted in order to optimize an experimental measure of splash, bounce, or coalescence. For example, one could run a number of ejections against suitable targets and use a digital camera to capture images of the process of droplet impact on the fluid at the targets for human or automatic analysis. Alternatively, one could use methods for scoring droplet coalescence from visual examination of the target after impact, for example by looking for multiple droplets where there should only be one if coalescence occurred.

Figure 4:
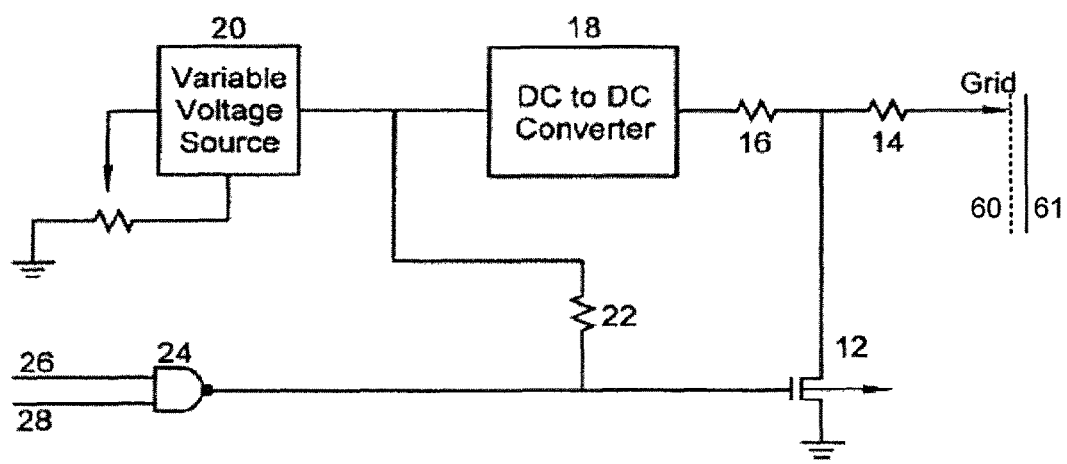
FIG. 4 depicts an exemplary circuit of the invention.

FIG. 4 depicts a particular embodiment of the circuit of the invention which is preferred. The fluid transport system in which this embodiment is used is an acoustic ejection system with droplets ejected upwards from a source reservoir to a target. In this embodiment the electrode is in the form of a grid, which is located behind the target. The source reservoir is maintained as an approximate ground by means of ionization, by the existence of true grounds in the vicinity, and/or by electrical conduction through the acoustic coupling medium.

As may be seen, the grid is driven by an N-type MOSFET 12 through a 5 MΩ resistor 14. When the voltage on the gate of the N-type MOSFET is high (above threshold), the grid is connected to ground via the 5 MΩ resistor 14. When the gate voltage is driven low, the grid is connected via resistor 14 and another 5 MΩ resistor 16 to the output of a DC to DC converter 18 which converts 0 to 5 V magnitudes to 0 to 1500 V. The voltage input of the DC to DC converter 18 is in turn connected to a variable voltage source 20 producing 0 to 5 V.

The gate of the N-type MOSFET 12 is connected via a 10 kΩ resistor 22 to the output of the variable voltage source 20. The gate is also driven by the output of a NAND gate 24 which allows two separate external control inputs 26 and 28 to set the gate low and thus disconnect the grid from ground, connecting it instead to the output of the DC to DC converted 18.

External logic (not shown) could employ the external inputs 26 and 28 to ensure that when the fluid transport system is loading well plates or the door is open, the grid is switched to ground via the N-type MOSFET 12. When droplet ejection starts, the control inputs could be used to bring the grid up to a fixed voltage between 500 and 1500 volts DC, with 800 V preferred. This voltage is applied evenly to the entire grid. This creates a weak static field that extends from the target plate to approximate ground planes in the drop ejection chamber and in the coupling fluid under the source plate wells. After drop transfer, the grid could be then switched back to ground. The grid is either completely on, or completely off.

As will be understood by those of skill in the art, the components in FIG. 4 would also have power supply connections which, as is common in electronics, are not explicitly shown.

In a variant on this preferred embodiment, the voltage alternates between positive and negative levels in order to prevent charge buildup on the target wells. Variants are also possible where the voltage is turned on during well plate loading and where the grid is left floating for some portion of the ejection cycle.

In an alternative preferred embodiment, an ionizer which creates a biased ion cloud is used to charge target well plates as they enter the system. The biased ion cloud is created, for example, by driving the ionizer with a suitably asymmetric or biased waveform. This ionizer could make use of standard ionization bars such as those made by Julie Industries (Wilmington, Mass.). The target well plate is then electrically isolated during the ejection cycle. The electric field modifying coalescence properties would be caused chiefly by the charge which was imparted to the target well plate by means of the biased ion cloud ionizer. Instead of imparting charge to the target well plate, it would be possible to charge an object placed near the target well plate as an alternative way of generating an electric field.

In another alternative preferred embodiment, a corona discharge which produces ions of a particular polarity in a localized portion of space may be used to charge a droplet. Preferably a stream of gas directs the ions produced by the corona discharge to the droplet. Alternatively, the droplet may pass through the discharge. In this case, preferably the corona discharge is stable, as for example between a pin and a plane.

Where an electric field is employed to improve droplet coalescence and that electric field charges the droplets, the transfer of a large number of such droplets into a single mass of fluid at the target may produce a significant net charge in that mass of fluid, which would tend to screen an applied electric field and reduce its beneficial effects. One can estimate the field that might be produced by the deposition of the droplet charge in the receiving mass of fluid. That charge would tend to spread across the receiving fluid meniscus as a surface charge sheet, so that if the diameter of the fluid is d, the charge density of the sheet would be $$\sigma = NQ/d^2$$

where N is the number of droplets transferred and Q is the charge per individual droplet. If we assume that the direction of droplet flight between source reservoir and target is the vertical z direction, that the field is produced by an electrode at voltage V above the target, and that the source is an approximate ground, we get the equation $$E = \sigma/\varepsilon_0 + [V/z_{tf} - \sigma/\varepsilon_0]/[1+(\varepsilon_0/\varepsilon_{tf})(z_{elect}/z_{tf}-1)]$$

Here $z_{elect}$ denotes the height of the electrode above the source fluid, $z_{tf}$ denotes the height of the target fluid meniscus above the source fluid, and $\varepsilon_{tf}$ represents the permittivity of the target fluid. For any aqueous target fluid, the quantity $\varepsilon_0/\varepsilon_{tf}$ would be much less than unity, and typically $z_{elect}/z_{tf}$ would be somewhat greater than unity. Thus, the quantity $(\varepsilon_0/\varepsilon_{tf})(z_{elect}/z_{tf}-1) \ll 1$, so that $1/[1+(\varepsilon_0/\varepsilon_{tf})(z_{elect}/z_{tf}-1)] \sim 1-(\varepsilon_0/\varepsilon_{tf})(z_{elect}/z_{tf}-1)$, and the electric field may be approximated as:

$$E \sim (V/z_{tf})[1-(\varepsilon_0/\varepsilon_{tf})(z_{elect}/z_{tf}-1)] + (\sigma/\varepsilon_{tf})(z_{elect}/z_{tf}-1)$$

The first term of this expression, $E_{init} = (V/z_{tf})[1-(\varepsilon_0/\varepsilon_{tf})(z_{elect}/z_{tf}-1)]$, is the field between source and target before any droplets arrive. The second term of this expression $E_{drop} = (\sigma/\varepsilon_{tf})(z_{elect}/z_{tf}-1)$ is the portion of the electric field due to the deposited charge at the meniscus. It is preferable, to avoid uncontrolled change in the actual electric field E, for $E_{drop}$ to be considerably less than $E_{init}$, for example ten times less. Applying again the fact that $(\varepsilon_0/\varepsilon_{tf})(z_{elect}/z_{tf}-1) \ll 1$, we have $$E_{drop}/E_{init} \sim (\sigma/\varepsilon_{tf})(z_{elect}/z_{tf})/V$$

If $Q = 1 \times 10^{-13}$ C, and d=3.5 mm, we have $\sigma = 8.16 \times 10^{-9}$ C/m² per droplet. If $z_{elect} - z_{tf} = 5$ mm, $\varepsilon_{tf} = 80\varepsilon_0$, and V=800 V, then the ratio $E_{drop}/E_{init} \sim (\sigma/\varepsilon_{tf})(z_{elect}-z_{tf})/V = 76 \times 10^{-6}$ per droplet. Thus, to keep this ratio below 1/10, it is desirable to deposit no more than 1300 droplets. If it is desired to deposit more than that number of droplets, it might be worthwhile reversing the direction of the electric field by reversing the polarity of V, so that charge of opposite polarity starts to neutralize the accumulated σ on the surface of the target fluid.

Variations of the present invention will be apparent to those of ordinary skill in the art. For example, the invention may be suitable for use with any of the performance enhancing features associated with acoustic technologies such those described in U.S. patent application Ser. No. 10/010,972, and Ser. No. 10/310,638, each entitled "Acoustic Assessment of Fluids in a Plurality of Reservoirs," filed Dec. 4, 2001 and Dec. 4, 2002, respectively, inventors Mutz and Ellson and U.S. patent application Ser. No. 10/175,375, entitled "Acoustic Control of the Composition and/or Volume of Fluid in a Reservoir," filed Jun. 18, 2002, inventors Ellson and Mutz. In addition, the invention may be used in a number of contexts such as handling pathogenic fluids (see U.S. patent application Ser. No. 10/199,907, entitled "Acoustic Radiation of Ejecting and Monitoring Pathogenic Fluids," filed Jul. 18, 2002, inventors Mutz and Ellson) and manipulating cells and particles (see U.S. Patent Application Publication Nos. 20020090720 and 20020094582).

It is to be understood that while the invention has been described in conjunction with the preferred specific embodiments thereof, that the foregoing description and the examples that follow are intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

The following examples are put forth so as to provide those of ordinary skill in the art with a complete disclosure and description of how to implement the invention, and are not intended to limit the scope of what the inventors regard as their invention.

EXAMPLE 1

Within an acoustic ejection system, a conducting plate was situated 7 mm above a 384 well plate in the source position (wells facing up). The 384 well plate contained 30 μL of 70% DMSO/30% water in all wells. The ejection of 2.5 nL drops was then captured on video, with 0 V and with 800 V applied to the upper plate. The acoustic coupling fluid, which contacts the bottom of the well plate, was held in contact with ground potential. The electric field with the electrode at 800 V is estimated to be 49,000 V/m based on a distance of 16.5 mm between the ground plane and the electrode. With electric field, the vertical position of the 2.5 nL drops was $\Delta z$=61 μm higher at t=6.6 ms after ejection, compared to having the upper electrode grounded.

It is hypothesized that the difference of position caused by the electric field was due to the droplet becoming charged during the ejection. To calculate the charge q imparted to the droplet we proceed as follows.

The forces on a droplet of charge q at position z and time t are $-gm$ for gravity, $qE$ for electric field, and, if Stokes' law applies, $-kv(t)$ for drag where $k=3\pi\eta n$, $\eta$ being the viscosity of air, $1.8\times10^{-5}$ kg-s/m, and d being the droplet diameter. Applying Newton's law, we get $$m\, d^2z/dt^2 = -gm + qE - k(dz/dt)$$

which can be rewritten as $$m\, dv/dt = -gm + qE - kv$$

where $v=dz/dt$ is the velocity of the droplet in the z direction.

In general, a linear first order differential equation $dv/dt+Av+B=0$ with $A\neq 0$ has the solution $$v(t)=(v_0+B/A)\exp(-tA)-Bt/A$$

where $v(0)=v_0$. Integrating;

$$z(t)=(1/A)(v_0+B/A)(1-\exp(-tA))-Bt/A$$

if z=0 at t=0. Here $A=k/m$ and $B=g-qE/m$. The difference between z(t) with the electric field E on and off is thus $$\Delta z = (1/A^2)(qE/m)(1-\exp(-tA)) - (qE/mA)t$$
$$= (1/A^2)(qE/m)(1-\exp(-tA)-tA),$$

so that $q=\Delta z(m/E)(A^2/(1-\exp(-tA)-tA))$. When $A\to 0$ (meaning the drag force$\to 0$), taking limits in the formula for q, we get the simpler formula $q=2\Delta z(m/Et^2)$.

The value m is about 2.7 μm given that the drop has a 2.5 nL volume and 70% DMSO/30% water has a density of about 1.07. Values for E have been given above. The droplet diameter is ~168 μm for a 2.5 nL sphere. We thus have A~10 $s^{-1}$ so that tA~0.066 (dimensionless). Substituting these values in the formula for q given above we get q~$1.6\times10^{-13}$ C.

The difference in velocities with and without the electric field is given by $\Delta v = qE/A(1-\exp(-tA))$~0.02 m/s. As may be seen, in this example the electric field had little effect on the velocity of the droplet, which is on the order of 2 m/s.

EXAMPLE 2

A study was carried out with an acoustic ejection system to better understand the influence of droplet speed on coalescence. A Krautkramer 15 MHz F2 lens was used, and 70% DMSO/30% water was ejected into an inverted target well, filled with NaOH buffer. The receiving fluid surface was slightly convex. Drops were ejected of nominal volume 5 nL, 2.5 nL, and 1.25 nL.

Figure 5A:
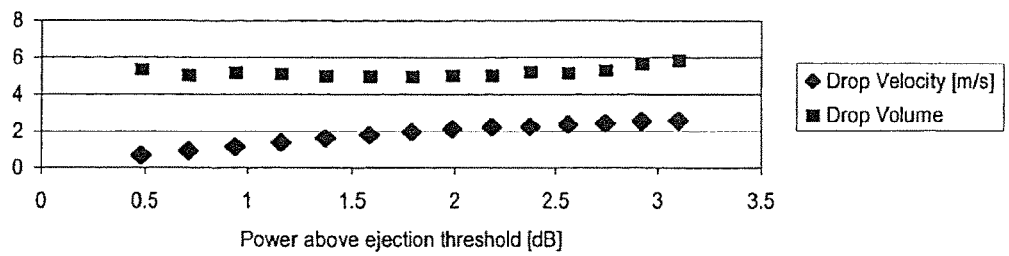
FIGS. 5A-5C show the speed control achievable through control of the acoustic energy in an acoustic ejection system.
Figure 5B:
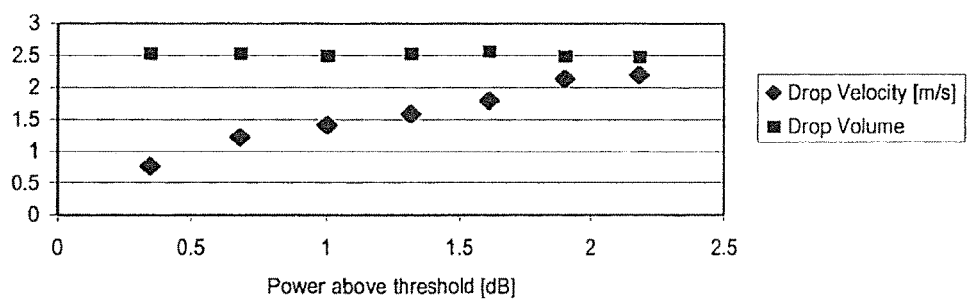
Figure 5C:
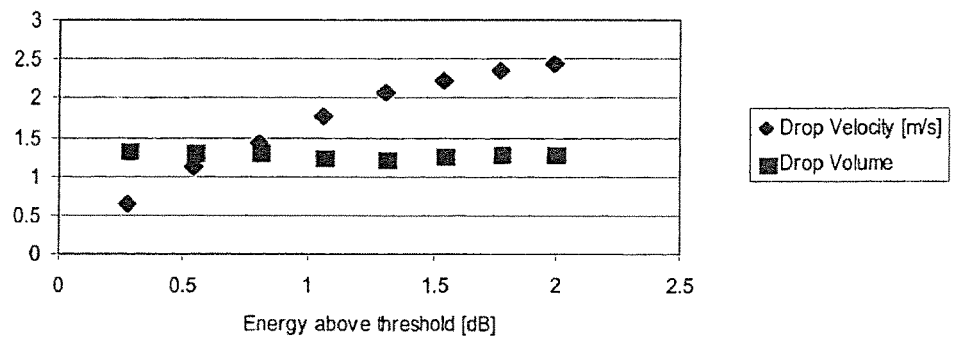

First, the drop volumes and velocities were extracted from video data, as a function of power above threshold. These are shown in FIGS. 5A through 5C.

In these graphs, the displayed power is based on the amplitude delivered to the acoustic transducer, which may be subject to saturation in the ranges indicated. The data span the entire range from ejection threshold (0 dB always corresponds to threshold) to satellite threshold, so that the data should represent well the operating window for each ejection condition. The drop velocities quoted in FIGS. 5A-5C are the initial velocities, directly above the source fluid.

Figure 6A:
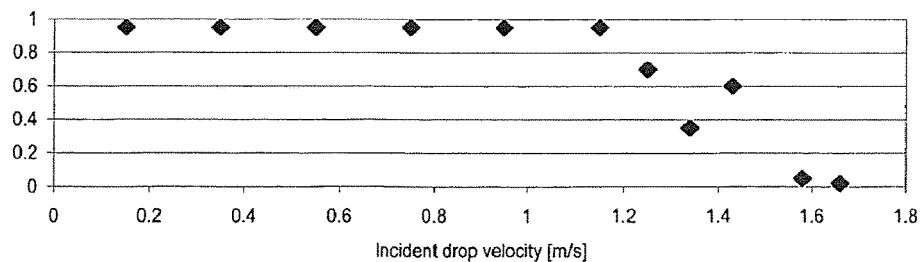
FIGS. 6A-6C show the effect of droplet speed on the likelihood of droplet coalescence for 70% DMSO/30% water.
Figure 6B:
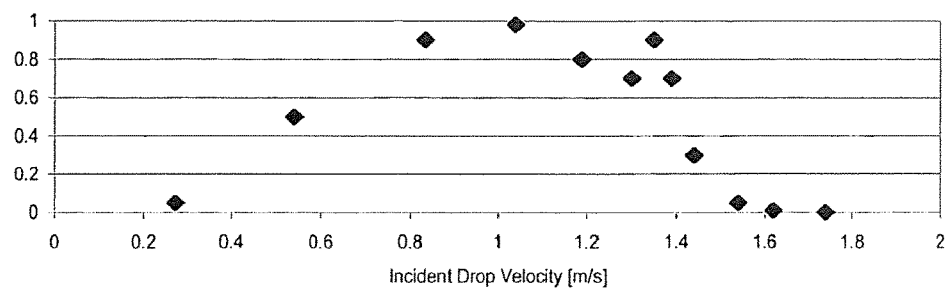
Figure 6C:
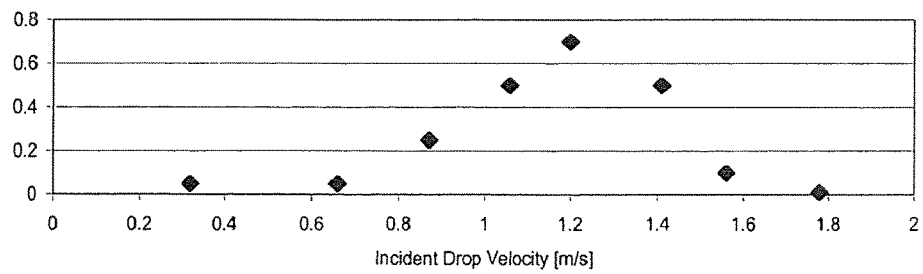

FIGS. 6A-6C show curves representing the drop bounce probability (from the filled 384 well), as a function of the incident drop velocity at the destination well. The velocities in these figures are velocities upon arrival at the destination well.

EXAMPLE 3

In a fluid transfer system based on acoustic ejection between well plates and having an electrode behind the target plate, metal foil was placed over the source plate, and holes were punctured to access the wells. This metal aperture over the source plate was then grounded, and acted to screen the applied electric field from the source well fluid (the field strength with the foil present would be less than 1% of that present without the foil). Thus there would be minimal droplet charging with the foil in place. With the foil present, the field between the source plate and the destination well fluid would actually be increased, however, so that a dipole-dipole interaction would be enhanced. It was found that with the foil present, there was essentially no reduction in droplet bounce when the 800V was applied to the grid behind the target plate.

EXAMPLE 4

A foil with apertures was used in the system of Example 3, but this time over the target plate rather than over the source plate. The foil was held at 800 V, as was the grid behind the target plate. With this arrangement, there is essentially no electric field present within the target plate wells, but there is drop charging, due to the electric field inside the source plate. It was found that for this scenario, there was excellent reduction in drop bounce.

We claim:

1. A method for transporting one or more droplets of one or more fluids from one or more reservoirs to contact one or more targets, the method comprising:
   generating acoustic radiation with an acoustic power level;
   ejecting a fluid droplet from a first fluid within a reservoir by the generated acoustic radiation;
   transporting the ejected fluid droplet at a droplet velocity towards a target;
   applying a predetermined electric field to the fluid droplet and the target, wherein applying the predetermined electric field comprises applying a voltage across first and second electrodes, the first electrode comprising a grid disposed behind the target;
   generating a dipole within the fluid droplet by the applied predetermined electric field; and
   attracting the fluid droplet to contact the target by an interaction between the dipole and the target;
   wherein the applying a predetermined electric field to the fluid droplet and the target is performed without substantially affecting the droplet velocity;
   wherein the attracting the fluid droplet to contact the target includes increasing, by the applied predetermined electric field, a likelihood that the fluid droplet does not splash or bounce on contacting the target.

2. The method of claim 1 wherein the transporting the ejected fluid droplet at a droplet velocity towards a target includes transporting the ejected fluid droplet upwards towards the target.

3. The method of claim 1 wherein the target is a second fluid on a substrate.

4. The method of claim 3 wherein the increasing, by the applied predetermined electric field, a likelihood that the fluid droplet does not splash or bounce on contacting the target includes increasing, by the applied predetermined electric field, a likelihood that the fluid droplet coalesces with the second fluid on the substrate.

5. The method of claim 1 wherein the applying a predetermined electric field to the fluid droplet and the target affects the droplet velocity by no more than 10% in magnitude.

6. The method of claim 5 wherein the applying a predetermined electric field to the fluid droplet and the target affects the droplet velocity by about 1% in magnitude.

7. The method of claim 1 wherein a first direction of the applied predetermined electric field and a second direction of the droplet velocity are the same.

8. The method of claim 1 wherein the applied predetermined electric field is oriented along a direction of the droplet velocity.

9. The method of claim 1, further comprising controlling, with a circuit, a voltage across electrodes generating the predetermined electric field such that the predetermined electric field substantially does not affect the droplet velocity and increases the likelihood that the fluid droplet does not splash or bounce on contacting the target.

10. A method for transporting one or more droplets of one or more fluids from one or more reservoirs to contact one or more targets, the method comprising:
   generating first acoustic radiation with a first acoustic power level;
   ejecting a first fluid droplet from a first fluid within a first reservoir by the generated first acoustic radiation;
   transporting the ejected first fluid droplet at a first droplet velocity towards a target;
   applying a predetermined first electric field to the first fluid droplet and the target, wherein applying the predetermined first electric field comprises applying a first voltage across first and second electrodes, the first electrode comprising a grid disposed behind the target;
   generating a first dipole within the first fluid droplet by the applied predetermined first electric field;
   attracting the first fluid droplet to contact the target by a first interaction between the first dipole and the target;
   generating second acoustic radiation with a second acoustic power level;
   ejecting a second fluid droplet from the first fluid within the first reservoir or from a second fluid within a second reservoir by the generated second acoustic radiation;
   transporting the ejected second fluid droplet at a second droplet velocity towards the target;
   applying a predetermined second electric field to the second fluid droplet and the target, wherein applying the predetermined second electric field comprises applying a second voltage across the first and second electrodes;
   generating a second dipole within the second fluid droplet by the applied predetermined second electric field;
   attracting the second fluid droplet to contact the target by a second interaction between the second dipole and the target;
   wherein:
      the applying a predetermined first electric field to the first fluid droplet and the target is performed without substantially affecting the first droplet velocity; and
      the attracting the first fluid droplet to contact the target includes increasing, by the applied predetermined first electric field, a first likelihood that the first fluid droplet does not splash or bounce on contacting the target;
   wherein:
      the applying a predetermined second electric field to the second fluid droplet and the target is performed without substantially affecting the second droplet velocity; and
      the attracting the second fluid droplet to contact the target includes increasing, by the applied predetermined second electric field, a second likelihood that the second fluid droplet does not splash or bounce on contacting the target.

11. The method of claim 10 wherein a first direction of the applied predetermined first electric field and a second direction of the applied predetermined second electric field are opposite to each other.

12. The method of claim 11 wherein:
   the first direction of the applied predetermined first electric field and a third direction of the first droplet velocity are directly opposite to each other; and
   the second direction of the applied predetermined second electric field and a fourth direction of the second droplet velocity are the same.

13. The method of claim 12 wherein the third direction of the first droplet velocity and the fourth direction of the second droplet velocity are the same.

14. The method of claim 11 wherein:
   the first direction of the applied predetermined first electric field and a third direction of the first droplet velocity are the same; and
   the second direction of the applied predetermined second electric field and a fourth direction of the second droplet velocity are directly opposite to each other.

15. The method of claim 14 wherein the third direction of the first droplet velocity and the fourth direction of the second droplet velocity are the same.

16. The method of claim 10 wherein the transporting the ejected first fluid droplet at a first droplet velocity towards a target includes transporting the ejected first fluid droplet upwards towards the target.

17. The method of claim 10 wherein the target is a third fluid on a substrate.

18. The method of claim 17 wherein the increasing, by the applied predetermined first electric field, a first likelihood that the first fluid droplet does not splash or bounce on contacting the target includes increasing, by the applied predetermined first electric field, a third likelihood that the first fluid droplet coalesces with the third fluid on the substrate.

19. The method of claim 17 wherein the increasing, by the applied predetermined second electric field, a second likelihood that the second fluid droplet does not splash or bounce on contacting the target includes increasing, by the applied predetermined second electric field, a fourth likelihood that the second fluid droplet coalesces with the third fluid on the substrate.

20. The method of claim 10 wherein the applying a predetermined first electric field to the first fluid droplet and the target affects the first droplet velocity by no more than 10% in magnitude.

21. The method of claim 20 wherein the applying a predetermined first electric field to the first fluid droplet and the target affects the first droplet velocity by about 1% in magnitude.

22. The method of claim 10 wherein:
the first fluid and the second fluid are the same.

23. The method of claim 10 wherein:
the first fluid and the second fluid are different.

24. The method of claim 10, further comprising controlling, with a circuit, a voltage across electrodes generating the predetermined first electric field such that the predetermined first electric field substantially does not affect the first droplet velocity and increases the likelihood that the first fluid droplet does not splash or bounce on contacting the target and further comprising controlling, with the circuit, a voltage across the electrodes generating the predetermined second electric field such that the predetermined second electric field substantially does not affect the second droplet velocity and increases the likelihood that the second fluid droplet does not splash or bounce on contacting the target.

25. A method for transporting one or more droplets of one or more fluids from one or more reservoirs to contact one or more targets, the method comprising:
generating acoustic radiation with an acoustic power level;
ejecting a fluid droplet from a first fluid within a reservoir by the generated acoustic radiation;
transporting the ejected fluid droplet at a droplet velocity towards a target;
applying a predetermined electric field to the fluid droplet and the target;
generating a dipole within the fluid droplet by the applied predetermined electric field; and
attracting the fluid droplet to contact the target by an interaction between the dipole and the target;
wherein the applying a predetermined electric field to the fluid droplet and the target is performed without substantially affecting the droplet velocity; and
wherein the attracting the fluid droplet to contact the target includes increasing, by the applied predetermined electric field, a likelihood that the fluid droplet does not splash or bounce on contacting the target;
the method further comprising reversing the applied predetermined electric field so as to neutralize accumulated charge at the target.

26. A method for transporting one or more droplets of one or more fluids from one or more reservoirs to contact one or more targets, the method comprising:
generating first acoustic radiation with a first acoustic power level;
ejecting a first fluid droplet from a first fluid within a first reservoir by the generated first acoustic radiation;
transporting the ejected first fluid droplet at a first droplet velocity towards a target;
applying a predetermined first electric field to the first fluid droplet and the target;
generating a first dipole within the first fluid droplet by the applied predetermined first electric field;
attracting the first fluid droplet to contact the target by a first interaction between the first dipole and the target;
generating second acoustic radiation with a second acoustic power level;
ejecting a second fluid droplet from the first fluid within the first reservoir or from a second fluid within a second reservoir by the generated second acoustic radiation;
transporting the ejected second fluid droplet at a second droplet velocity towards the target;
applying a predetermined second electric field to the second fluid droplet and the target;
generating a second dipole within the second fluid droplet by the applied predetermined second electric field;
attracting the second fluid droplet to contact the target by a second interaction between the second dipole and the target;
wherein:
the applying a predetermined first electric field to the first fluid droplet and the target is performed without substantially affecting the first droplet velocity; and
the attracting the first fluid droplet to contact the target includes increasing, by the applied predetermined first electric field, a first likelihood that the first fluid droplet does not splash or bounce on contacting the target;
wherein:
the applying a predetermined second electric field to the second fluid droplet and the target is performed without substantially affecting the second droplet velocity; and
the attracting the second fluid droplet to contact the target includes increasing, by the applied predetermined second electric field, a second likelihood that the second fluid droplet does not splash or bounce on contacting the target;
the method further comprising reversing the applied predetermined first electric field so as to neutralize accumulated charge at the target.

27. The method of claim 26, further comprising reversing the applied predetermined second electric field so as to neutralize accumulated charge at the target.

* * * * *